US00PP34396P2

(12) United States Plant Patent
Hansen

(10) Patent No.: US PP34,396 P2
(45) Date of Patent: Jun. 28, 2022

(54) ***SEDUM* PLANT NAMED 'BRIGHT IDEA'**

(50) Latin Name: ***Sedum kamtschaticum* (Fisch.)**
Varietal Denomination: Bright Idea

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/803,136

(22) Filed: Mar. 1, 2022

(51) Int. Cl.
*A01H 5/12* (2018.01)
*A01H 6/32* (2018.01)

(52) U.S. Cl.
USPC ..... Plt./479

(58) Field of Classification Search
USPC ..... Plt./479
CPC ... A01H 5/02; A01H 5/12; A01H 5/00; A01H 6/32; A01H 6/328
See application file for complete search history.

*Primary Examiner* — June Hwu

(57) ABSTRACT

The new and distinct cultivar of perennial *Sedum* plant named 'Bright Idea' is characterized by drought-tolerant, winter-hardy, tight, compact, rounded mounds, flower stems that remain upright in the center of the plant throughout the growing season, small, medium-green, glossy foliage with reddish blush along the edges and numerous bright yellow flowers clustered on small heads, on bright reddish stems, that completely covering the plant in early summer.

2 Drawing Sheets

Botanical designation: *Sedum kamtschaticum* (Fisch.).
Cultivar denomination: 'Bright Idea'.

STATEMENT REGARDING PRIOR DISCLOSURES UNDER 37 CFR 1.77(b)(6)

The first public disclosure of the claimed plant was the non-enabling photograph and brief description on a website operated by Walters Gardens, Inc. on Dec. 1, 2021. Prior to that the claimed plant was first sold privately to Prides Corner Farms on Apr. 5, 2021, by Walters Gardens, Inc., who obtained the plant and all information relating thereto, from the inventor. No plants of *Sedum* 'Bright Idea' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Sedum* or stonecrop plant, botanically known as *Sedum* and hereinafter referred to by the cultivar name 'Bright Idea'. The new plant is a single seedling selection from a cross performed by the inventor between two proprietary, unreleased, hybrids at a trial garden or a wholesale perennial nursery in Zeeland, Mich., USA. The female or seed parent was known only by the breeder code 14-40-1 (not patented) and the male or pollen parent was known only by the breeder code 14-23-4. The cross was made on Jun. 13, 2017. The individual plant ultimately named 'Bright Idea' was given the breeder code 16-13-8 during the evaluation process at the same nursery in Zeeland, Mich.

Asexual reproduction of *Sedum* 'Bright Idea' by division in summer of 2018, followed by vegetative cuttings since the summer of 2019 at a wholesale perennial nursery in Zeeland, Mich., USA has shown that the unique features of this new *Sedum* plant are stable and reproduced true to type in successive generations.

SUMMARY OF THE INVENTION

Plants of *Sedum* 'Bright Idea' have not been observed under all possible environmental conditions. The phenotype may vary somewhat with variations in environment such as temperature, available water, fertility and light intensity without, however, any variation in genotype.

The following traits have been repeatedly observed and are determined to be the unique characteristics of *Sedum* 'Bright Idea'. The following characteristics in combination distinguish 'Bright Idea' as a new and distinct *Sedum* plant unique from all other Stonecrop plants known to the inventor:

1. Compact, rounded mound plant habit.
2. Small, medium-green, glossy foliage produced on short stiff stems.
3. Leaf margins developing slight reddish blush in high light conditions.
4. Stems develop a bright reddish color in high light.
5. Numerous, bright yellow flowers in clusters nearly completely cover the plant in early summer.
6. Plants are drought tolerant and winter hardy to at least USDA zone 3.

The female parent has a taller habit and more prone to lodging. The male parent is more compact and shorter in habit.

Other similar plants include: 'Little Miss Sunshine' U.S. Plant Pat. No. 30,039, 'Yellow Brick Road' U.S. Plant Pat. No. 32,158 and 'Weihenstephaner Gold' (not patented).

'Little Miss Sunshine' has a shorter and flatter habit, has green stems and slightly smaller foliage. 'Yellow Brick Road' has a shorter and flatter habit, sightly smaller foliage and stems are not as bright reddish-colored. 'Weihenstephaner Gold' is also smaller in habit, with leaves and flower buds that are more bronze tinted and stems that are more greyed-purple. Compared to the *S. kamtschaticum* in the trade, the new plant has red stems, is taller in habit and forms a tighter clumping mound.

BRIEF DESCRIPTION OF THE PHOTOGRAPH

The photograph of the new plant demonstrates the unique traits and the overall appearance of *Sedum* 'Bright Idea'. The colors are as accurate as reasonably possible with color reproductions of this type. Variations in ambient light spectrum, source and direction may cause the appearance of minor variation in color. The plants used in the photographs were two-year-old plants grown in an open, full-sun trial garden at a wholesale perennial nursery in Zeeland, Mich. with supplemental water and fertilizer when needed. No plant growth regulators have been used.

DETAILED BOTANICAL DESCRIPTION

Figure 1:
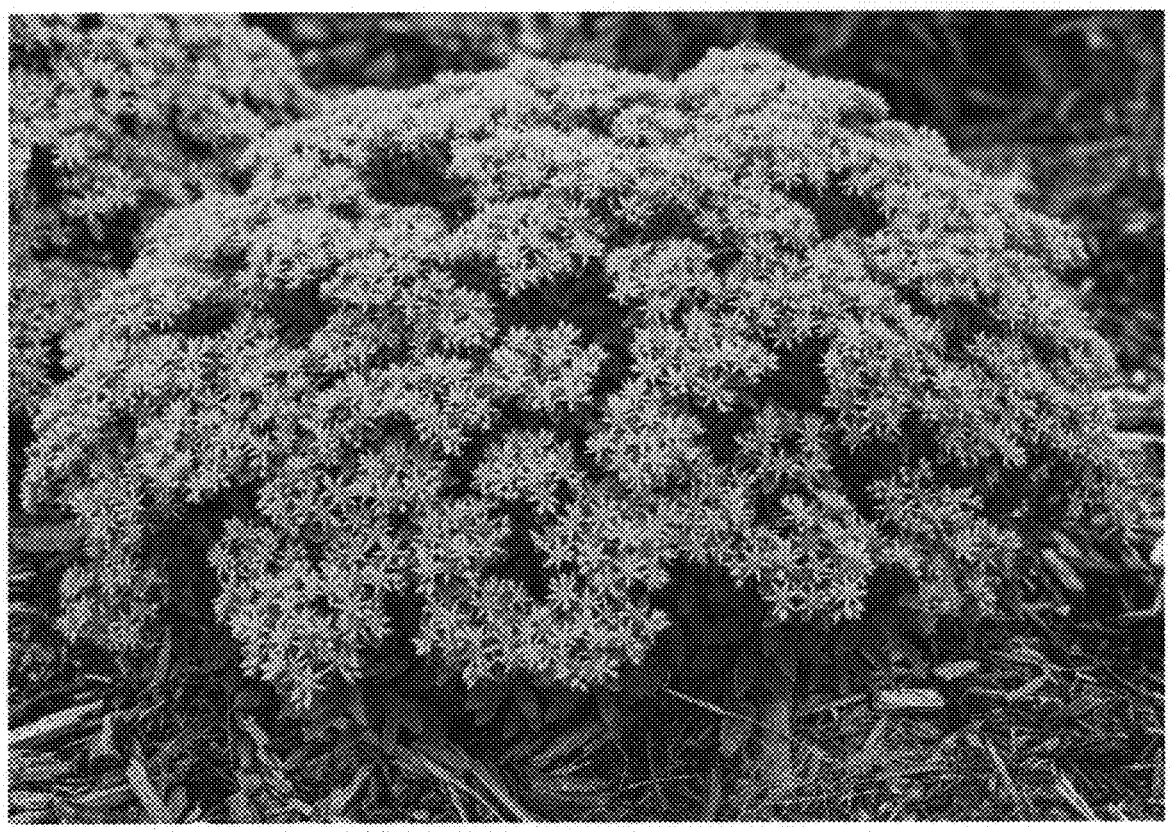
FIG. 1 shows the plant in full flower habit.
Figure 2:
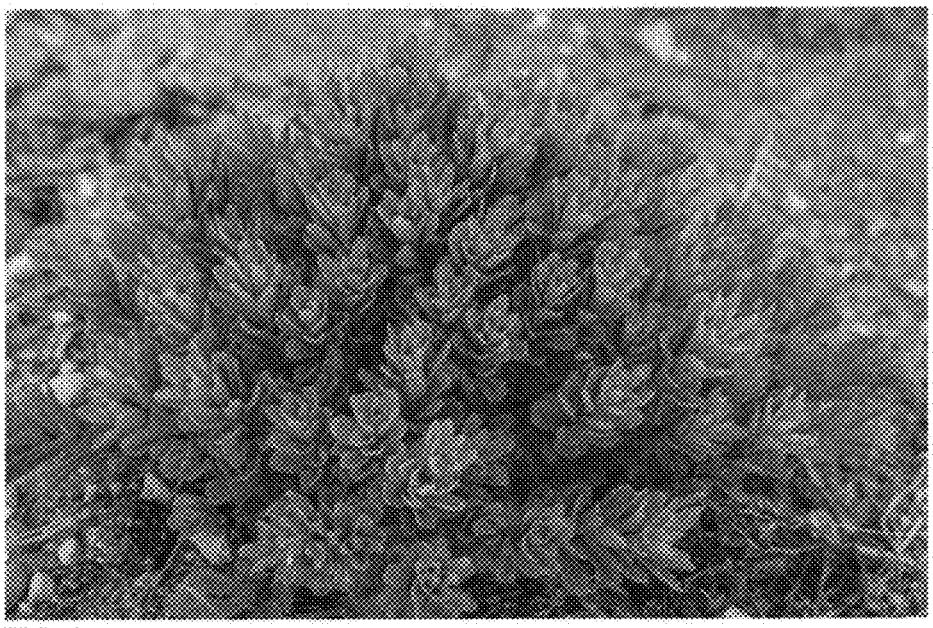
FIG. 2 shows a close-up of the foliage growing in intense light.
Figure 3:
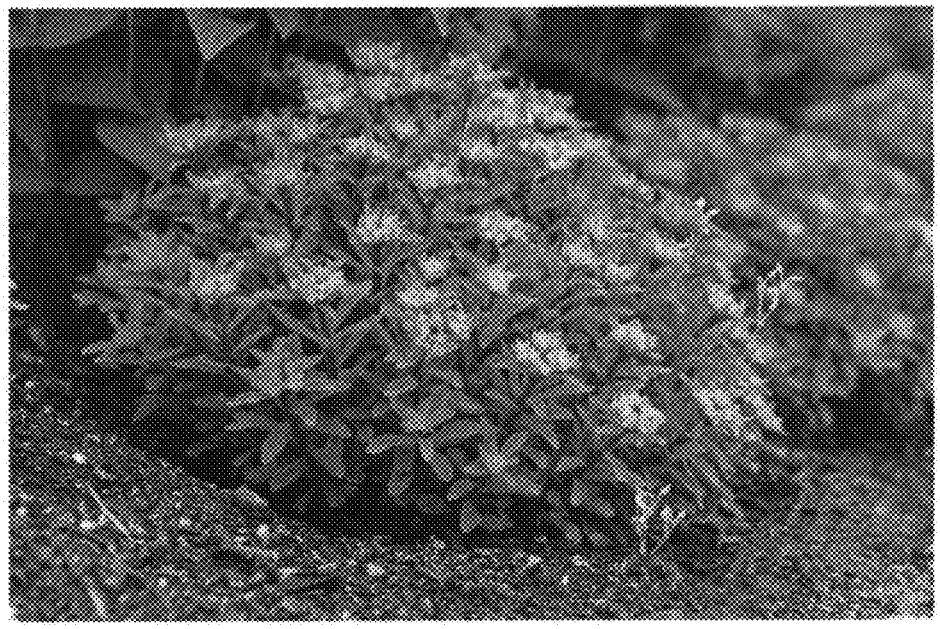
FIG. 3 show the plant in early bud stages with reddish stems.

The following is a detailed description of two-year-old plants of the new cultivar as grown outdoors in a full sun trial plot at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Parentage: The female or seed parent is 14-40-1, the male or pollen parent is 14-23-4;

Asexual propagation: Stem cuttings and division;

Time to initiate roots: About two weeks;

Time to finish a 3.7-liter flowering container: About three months in the summer from a rooted 2.5 cm plug;

Root description: Moderate thickness, slightly fleshy; freely branching; creamy white to light tan in color; color nearest RHS NN155B;

Plant habit: Winter-hardy, succulent, herbaceous perennial; low mounded; about 70 to 90 stiff stems per plant, upright to outright, arising from a dense base; flower heads freely branching; dense;

Growth rate: Vigorous;

Plant size: To about 29.0 cm tall and 48.0 cm wide in full flower; foliage to about 25 cm tall and 45 cm wide;

Main stems: Cylindrical; glabrous; semi-lustrous; about 70 to 90 per plant; diameter at base about 4.0 mm, about 24 cm long from base to initial flower cymes; maintaining foliage in distal half of stem; internodes average about 0.4 mm; about 54 nodes in 24 cm;

Main stem color: Variable; proximal one-half blend between RHS 176B and RHS 191A, distally nearest RHS 146D with moderate to heavy maculate nearest RHS 187C to nearly solid RHS 53A;

Lateral branches: Typically from base or distal region; semi-lustrous; to about 2.0 mm diameter and about 7.0 cm long;

Lateral branch color: Nearest RHS 146D with moderate to heavy maculate nearest RHS 187C to nearly solid RHS 53A;

Foliage: Dextrose; held upright to about 60 degrees above horizontal; simple; oblanceolate; smooth; glabrous and matte abaxial and adaxial; base sessile and attenuate; apex acute; margin entire in proximal one-half and dentate in distal one-half, with about four to seven irregular flexible teeth from 0.5 mm long to 2.0 mm long; fleshy and succulent;

Leaf size: To about 43.0 mm long and about 12.0 mm across near apex, average about 36.0 mm long, about 10.0 mm across at widest portion near apex, base tapering to about 2.0 mm across; about 1.5 mm thick;

Foliage color: Young developing leaves—adaxial distally nearest RHS 148C, base nearest RHS 145B, abaxial distally nearest RHS 148C with base nearest RHS 145B; fully developed leaves at flowering time—adaxial nearest RHS NN137B, abaxial nearest RHS 191B; mature leaves in late summer—adaxial nearest RHS NN137B with teeth and apices nearest RHS 153D and heavily maculate with nearest RHS 44A, abaxial nearest RHS 191B with teeth and apices nearest RHS 18C and lightly maculate along edges with nearest RHS 42B;

Venation: Pinnate; color same as surrounding leaf tissue on both surfaces;

Flower: Rotate; upright; perfect; complete; rotate; actinomophic; sessile; in terminal compound cymes; freely flowering habit with up to 75 flower buds and flowers per terminal branched cyme, and 5,000 per plant, covering nearly the entire foliage in peak flower;

Flower size: About 14.0 mm across and 7.0 mm long;

Flower facing: Upwardly to outwardly;

Flower fragrance: Not detected;

Flowering season: Beginning early summer and continuing for about four weeks in Zeeland, Mich.;

Longevity: Individual flower remain effective for about four to six days on the plant; individual flowers persistent;

Flower buds about one day prior to opening: Broadly elliptic; apex acute; base rounded; about 7.0 mm long and 3.0 mm across;

Flower bud color: Exposed petals nearest RHS 9A distally and centrally and proximally nearest RHS 1C;

Inflorescence: About 5.0 cm tall from first branch and 5.0 cm across; to about 75 flowers per center cyme and 17 per cyme branch;

Petals: Typically six; lanceolate; acute apex, base truncate and fused, margin entire, glabrous; lustrous both adaxial and abaxial; typically about 7.0 mm long and about 2.0 mm across near middle;

Petal color: Adaxial nearest RHS 6A with midrib nearest RHS 1A; and abaxial nearest RHS 6C with midrib nearest RHS 1C;

Calyx: Campanulate; about 8.0 mm wide and 2.0 mm deep;

Sepals: Typically six, lanceolate to linear; margin entire; glabrous and lustrous abaxial and adaxial; acute apex; base truncate, fused in basal 1.0 mm; about 4.0 mm long and about 1.0 mm wide at fused base;

Sepal color: Nearest RHS 138A both adaxial and abaxial surfaces with base nearest RHS 145C;

Peduncles: Glabrous; cylindrical; strong and stiff, yet flexible; freely branching; angle erect in center to nearly 60 degrees above horizontal for branched portions; flowering portion about 5.0 cm long and 5.0 cm across;

Peduncle color: Variable; nearest RHS 146C and RHS 43B;
Pedicels: Sessile;
Androecium: Typically twelve; to 5.0 mm long;
*Filaments.*—Thin; cylindrical; upright; fused to petal base; about 4.0 mm long and about 0.3 mm diameter; color between RHS 145C and RHS 1C;
*Anthers.*—Ellipsoidal; basifixed; longitudinal; about 1.0 mm long and about 0.5 mm wide; color nearest RHS 153D;
*Pollen.*—Abundant; color nearest RHS 14A;
Gynoecium: Typically six; cylindrical, conical in distal one third; about 4.0 mm long;
*Style.*—Six; about 2.0 mm long and 0.5 mm diameter at point of attachment to ovary; glabrous; color nearest RHS 1A;
*Stigma.*—Six; minute; color nearest 145B;
*Ovary.*—Six; nearly cylindrical, tapering at apex to style; about 2.0 mm long and 1.0 mm diameter; color nearest RHS 145B;
Seed and fruit: Have not yet been observed;
Disease and pest resistance: Plants of the new *Sedum* 'Bright Idea' grow best with good drainage, full sun and moderate to low fertility. 'Bright Idea' is cold hardy from USDA zones 3 to 9. 'Bright Idea' tolerates heavy rains and wind and does not easily open in the center later in the season as many other stonecrop cultivars do. Other pest and disease resistance and tolerance outside that normal for stonecrop is not known.

It is claimed:

1. The new and distinct perennial *Sedum* plant named 'Bright Idea' as herein described and illustrated useful for landscaping as a specimen plant, en masse.

* * * * *